(12) United States Patent
Perkins (10) Patent No.: US 10,145,675 B2
(45) Date of Patent: Dec. 4, 2018

(54) USING TUNABLE LASERS IN THE DESIGN, MANUFACTURE, AND IMPLEMENTATION OF INTEGRATED OPTICAL ELEMENTS

(71) Applicant: Halliburton Energy Services, Inc., Houston, TX (US)

(72) Inventor: David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 467 days.

(21) Appl. No.: 14/408,354

(22) PCT Filed: Dec. 19, 2013

(86) PCT No.: PCT/US2013/076448
§ 371 (c)(1),
(2) Date: Dec. 16, 2014

(87) PCT Pub. No.: WO2015/094264
PCT Pub. Date: Jun. 25, 2015

(65) Prior Publication Data
US 2016/0258741 A1 Sep. 8, 2016

(51) Int. Cl.
*G01B 11/06* (2006.01)
*H01S 3/108* (2006.01)
*H01S 3/13* (2006.01)
*G01N 21/39* (2006.01)
*G01N 21/21* (2006.01)
(Continued)

(52) U.S. Cl.
CPC ........ *G01B 11/0675* (2013.01); *G01N 21/211* (2013.01); *G01N 21/39* (2013.01); *G01N 21/8422* (2013.01); *H01S 3/1083* (2013.01); *H01S 3/13* (2013.01); *G01J 4/04* (2013.01)

(58) Field of Classification Search
CPC ..... H01S 3/13; H01S 3/1083; G01N 21/8422; G01N 21/211; G01N 21/39; G01J 4/04
See application file for complete search history.

(56) References Cited

U.S. PATENT DOCUMENTS 5,152,296 A * 10/1992 Simons ................ A61B 5/0205
600/483
8,575,541 B1 11/2013 Jamison et al.
(Continued)

OTHER PUBLICATIONS

International Search Report and Written Opinion for PCT/US2013/076448 dated Sep. 17, 2014.

*Primary Examiner* — Dominic J Bologna
(74) *Attorney, Agent, or Firm* — Gilliam IP LLC (57) ABSTRACT

Disclosed are systems and methods that use a tunable laser during optical thin-film fabrication. One disclosed system includes a tunable laser capable of generating electromagnetic radiation, one or more thin-film devices arranged to receive the electromagnetic radiation, each thin-film device including one or more optical layers deposited on a corresponding substrate and configured to generate optically interacted radiation upon receiving the electromagnetic radiation, and an optical transducer arranged to receive the optically interacted radiation from each of the one or more thin-film devices and configured to generate output signals corresponding to the optically interacted radiation received from each of the one or more thin-film devices.

21 Claims, 3 Drawing Sheets

(51) Int. Cl.
*G01N 21/84* (2006.01)
*G01J 4/04* (2006.01)

(56) References Cited

U.S. PATENT DOCUMENTS

| | | | |
|---|---|---|---|
| 2002/0109100 A1* | 8/2002 | Jackson, III | G01N 21/6456 250/458.1 |
| 2006/0078998 A1* | 4/2006 | Puskas | G01N 21/6428 436/64 |
| 2008/0094631 A1* | 4/2008 | Jung | A61B 5/0075 356/419 |
| 2009/0268203 A1 | 10/2009 | Uzunbajakava et al. | |
| 2010/0096561 A1* | 4/2010 | Johnson | G01N 21/6428 250/459.1 |
| 2010/0245096 A1 | 9/2010 | Jones et al. | |
| 2010/0245819 A1* | 9/2010 | Li | G01B 11/0641 356/327 |
| 2013/0034842 A1 | 2/2013 | Tunheim et al. | |
| 2013/0162999 A1* | 6/2013 | Myrick | G01J 3/4406 356/416 |
| 2013/0284894 A1 | 10/2013 | Freese et al. | |

* cited by examiner

USING TUNABLE LASERS IN THE DESIGN, MANUFACTURE, AND IMPLEMENTATION OF INTEGRATED OPTICAL ELEMENTS

The present application is a national stage entry from International Application No. PCT/US2013/076448, filed on Dec. 19, 2013 and entitled "Using Tunable Lasers in the Design, Manufacture, and Implementation of Integrated Optical Elements."

BACKGROUND

The present disclosure relates to optical thin films and, more particularly, to systems and methods of using tunable lasers in the design, manufacture and implementation of optical thin films.

Optical computing devices, also commonly referred to as "opticoanalytical devices," can be used to analyze and monitor a substance in real time. Such optical computing devices will often employ a light source emitting electromagnetic radiation that reflects or refracts from a substance and optically interacts with an optical processing element to determine quantitative and/or qualitative values of one or more physical or chemical properties of the substance. The optical element may be, for example, an integrated computational element (ICE), also known as a multivariate optical element (MOE), which may act as an optical interference filter that can be designed to operate over a continuum of wavelengths in the electromagnetic spectrum from the UV to mid-infrared (MIR) ranges, or any sub-set of that region. Electromagnetic radiation that optically interacts with the substance is changed and processed by the ICE so as to be readable by a detector, such that an output of the detector can be correlated to the physical or chemical property of the substance being analyzed.

An exemplary ICE (hereafter "ICE core") typically includes a plurality of optical layers consisting of various materials whose index of refraction and size (e.g., thickness) may vary between each layer. The design of an ICE core (referred to herein as an "ICE design") refers to the number and thicknesses of the respective layers of the ICE core. The layers may be strategically deposited and sized so as to selectively pass predetermined fractions of electromagnetic radiation at different wavelengths configured to substantially mimic a regression vector corresponding to a particular physical or chemical property of interest of a substance. Accordingly, an ICE design will exhibit a transmission function that is weighted with respect to wavelength. As a result, the output light from the ICE core conveyed to the detector may be related to the physical or chemical property of interest for the substance.

Ellipsometry is an optical measurement technique that may be used in the design and fabrication of optical processing elements, such as ICE cores or other optical thin films. For example, during fabrication, ellipsometry may be used to monitor the progress of the deposition process to ensure that parameters of the optical thin films are within specification of the thin-film design. Similar to the workings of an optical computing device, ellipsometry uses a light source that emits electromagnetic radiation to optically interact with a layer of the optical processing elements deposited on a substrate, thereby generating reflected electromagnetic radiation that may be used to measure or characterize the layer. Example characterization information that may be measured may include, but is not limited to, surface roughness, layer thickness, and refractive index of the thin film layer or design. The light source used in the ellipsometry measurement system greatly affects what information is determinable and the accuracy thereof. Typical light sources used in ellipsometry measurement systems include broadband light sources, such as a Tungsten-filament lamp or a light bulb.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure relates to optical thin films and, more particularly, to systems and methods of using tunable lasers in the design, manufacture and implementation of optical thin films.

The present disclosure provides improved systems and methods for characterizing layers of optical thin-films, such as layers of integrated computational element (ICE) cores, during fabrication through the use of tunable lasers in ellipsometry measurement systems. In one embodiment, an optical parametric oscillator (OPO) may be an integral part of the tunable laser and may enable tuning of the output wavelength. Advantageously, utilizing tunable lasers may result in signals having a higher signal-to-noise ratio (SNR), thus resulting in more accurate measurements. Moreover, a higher SNR may enable testing of low average transmittance ICE core designs, previously unmeasureable and therefore discarded, and further enable increased optical path length during fabrication. Resulting therefrom, in-situ spectroscopic measurements may be performed, as compared to previous ex-situ spectral measurements.

The systems and methods disclosed herein also include using tunable lasers to determine characteristics or analytes of a fluid, such as one or more chemical compositions present within the fluid. Advantageously, the increased light flux of the tunable laser allows increased signal-to-noise ratios (SNR) on optical transducers, which may allow measurements that are more accurate. Additionally, the tunable laser may be selectively tuned by an operator to cover only discontinuous wavelengths, such as one or more wavelengths of interest in a sample under study.

The presently described systems and methods also disclose the implementation of tunable lasers to determine the transmittance of "optically thick" films or fluids. An "optically thick" fluid may be a fluid that exhibits a low transmittance of light, thus typically resulting in a small or an immeasurable amount of light being transmitted through the fluid. The high intensity light output of the tunable laser, however, may enable a measurable amount of light to be transmitted from the fluid, thus enabling previously unavailable measurements of transmittance for optically thick fluids.

The disclosed systems and methods may be suitable for the design and fabrication of ICE cores. However, it will be appreciated that the various disclosed systems and methods are equally applicable to fabrication of any thin-film used in thin-film applications. Such application areas and technology fields may include, but not limited to, the oil and gas industry, food and drug industry, industrial applications, the mining industry, the optics industry, the eyewear industry, and the electronics industry.

As used herein, the term "characteristic" refers to a chemical, mechanical, or physical property of a substance. The characteristic of a substance may include a quantitative or qualitative value of one or more chemical constituents or compounds present therein or any physical property associated therewith. Such chemical constituents and compounds may be referred to herein as "analytes." Illustrative characteristics of a substance that can be detected with the ICE cores described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, transmittance, combinations thereof, state of matter (solid, liquid, gas, emulsion, mixtures, etc.), and the like.

As used herein, the term "substance," or variations thereof, refers to at least a portion of matter or material of interest to be tested or otherwise evaluated using the ICE cores described herein. The substance includes the characteristic of interest, as defined above. The substance may be any fluid capable of flowing, including particulate solids, liquids, gases (e.g., air, nitrogen, carbon dioxide, argon, helium, methane, ethane, butane, and other hydrocarbon gases, hydrogen sulfide, and combinations thereof), slurries, emulsions, powders, muds, glasses, mixtures, combinations thereof, and may include, but is not limited to, aqueous fluids (e.g., water, brines, etc.), non-aqueous fluids (e.g., organic compounds, hydrocarbons, oil, a refined component of oil, petrochemical products, and the like), acids, surfactants, biocides, bleaches, corrosion inhibitors, foamers and foaming agents, breakers, scavengers, stabilizers, clarifiers, detergents, a treatment fluid, fracturing fluid, a formation fluid, or any oilfield fluid, chemical, or substance as found in the oil and gas industry. The substance may also refer to a solid material such as, but not limited to, rock formations, concrete, solid wellbore surfaces, and solid surfaces of any wellbore tool or projectile (e.g., balls, darts, plugs, etc.).

As used herein, the term "electromagnetic radiation" refers to radio waves, microwave radiation, terahertz, infrared and near-infrared radiation, visible light, ultraviolet light, X-ray radiation and gamma ray radiation.

As used herein, the term "optically interact" or variations thereof refers to the reflection, transmission, scattering, diffraction, or absorption of electromagnetic radiation either on, through, or from one or more processing elements (i.e., an ICE core or other optical thin film), a substance being analyzed by the processing elements, or a polarizer. Accordingly, optically interacted light refers to electromagnetic radiation that has been reflected, transmitted, scattered, diffracted, or absorbed by, emitted, or re-radiated, for example, using a processing element, but may also apply to optical interaction with a substance or a polarizer.

Figure 1:
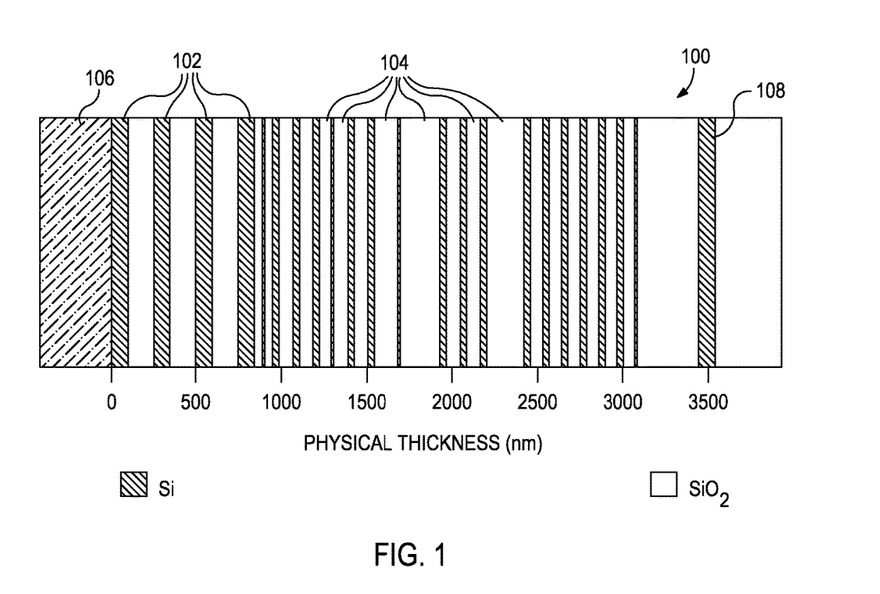
FIG. 1 illustrates an exemplary integrated computation element, according to one or more embodiments.

In operation, an ICE core is capable of distinguishing electromagnetic radiation related to a characteristic of interest of a substance from electromagnetic radiation related to other components of the substance. Referring to FIG. 1, illustrated is an exemplary ICE core 100, according to one or more embodiments of the present disclosure. As illustrated, the ICE core 100 may include a plurality of alternating layers 102 and 104, such as silicon (Si) and $SiO_2$ (quartz), respectively. In general, these layers 102, 104 consist of materials whose index of refraction is high and low, respectively. Other examples of materials might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE core 100 may include a layer 108 that is generally exposed to the environment of the device or installation, and may be able to detect a sample substance. The number of layers 102, 104 and the thickness of each layer 102, 104 are determined from the spectral attributes acquired from a spectroscopic analysis of a characteristic of the substance being analyzed using a conventional spectroscopic instrument. The spectrum of interest of a given characteristic typically includes any number of different wavelengths.

It should be understood that the exemplary ICE core 100 in FIG. 1 does not in fact represent any particular ICE core configured to detect a specific characteristic of a given substance, but is provided for purposes of illustration only. Consequently, the number of layers 102, 104 and their relative thicknesses, as shown in FIG. 1, bear no correlation to any particular substance or characteristic thereof. Nor are the layers 102, 104 and their relative thicknesses necessarily drawn to scale, and therefore should not be considered limiting of the present disclosure.

In some embodiments, the material of each layer 102, 104 can be doped or two or more materials can be combined in a manner to achieve the desired optical characteristic. In addition to solids, the exemplary ICE core 100 may also contain liquids and/or gases, optionally in combination with solids, in order to produce a desired optical characteristic. In the case of gases and liquids, the ICE core 100 can contain a corresponding vessel (not shown), which houses the gases or liquids. Exemplary variations of the ICE core 100 may also include holographic optical elements, gratings, piezoelectric, light pipe, and/or acousto-optic elements, for example, that can create transmission, reflection, and/or absorptive properties of interest.

The multiple layers 102, 104 may exhibit different refractive indices. By properly selecting the materials of the layers 102, 104 and their relative thickness and spacing, the ICE core 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrum of the characteristic or analyte of interest. These methods may include inverse Fourier transform (IFT) of the optical transmission spectrum and structuring the ICE core 100 as the physical representation of the IFT. The approximations convert the IFT into a structure based on known materials with constant refractive indices.

The weightings that the layers 102, 104 of the ICE core 100 apply at each wavelength may be set to the regression weightings described with respect to a known equation, data, or spectral signature. For instance, when electromagnetic radiation interacts with a substance, unique physical and chemical information about the substance may be encoded in the electromagnetic radiation that is reflected from, transmitted through, or radiated from the substance. This information is often referred to as the spectral "fingerprint" of the substance. The ICE core 100 may be configured to perform the dot product of the received electromagnetic radiation and the wavelength dependent transmission function of the ICE core 100. The wavelength dependent transmission function of the ICE core 100 is dependent on the material refractive index of each layer, the number of layers 102, 104 and thickness of each layer 102, 104. Thus, it can be appreciated that performing spectroscopic measurements on the layers 102, 104 during fabrication may indicate proper or improper refractive indexes and layer 102, 104 thicknesses, and further enable correction adjustments as necessary for proper operation of the ICE core 100 upon fabrication completion.

Figure 2:
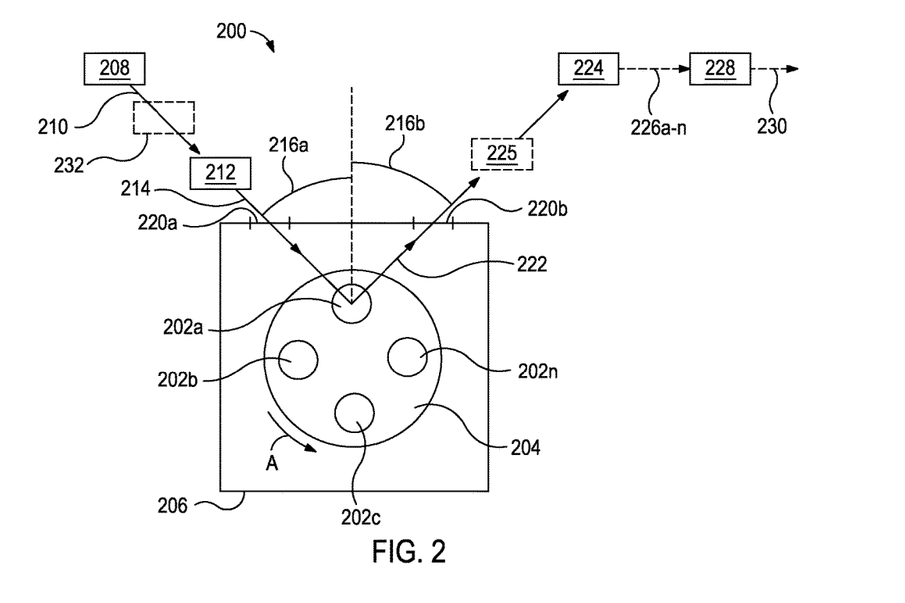
FIG. 2 illustrates an exemplary measurement system used during the fabrication of a thin-film device, according to one or more embodiments.

Referring now to FIG. 2, illustrated is an exemplary measurement system 200 that may be used during the fabrication of thin-film devices, according to one or more embodiments. As illustrated, the measurement system 200 may be configured to perform optical measurement techniques based on ellipsometry. More particularly, the measurement system 200 may be configured to perform ellipsometric measurements on one or more ICE cores 202 (shown as 202a, 202b, 202c, . . . 202n) arranged on an assembly 204 within a fabrication housing 206. Each ICE core 202a-n may be somewhat similar to the ICE core 100 of FIG. 1, and therefore will not be described again in detail.

The measurement system 200 may, for example, be configured to measure various parameters of the ICE cores 202a-n as they are being built within the fabrication housing 206. For instance, the measurement system 200 may be configured to estimate or otherwise determine the refractive index or thickness of each layer 102, 104 (FIG. 1) as it is deposited on its corresponding substrate 106 (FIG. 1) for each ICE core 202a-n. One of skill in the art will appreciate that, while ICE cores 202a-n are depicted and discussed herein, the ICE cores 202a-n may be replaced and the techniques disclosed herein may be equally applied to ellipsometry measurements of fluids (i.e., gas(es) or liquid(s)) or thin-film devices in general.

The measurement system 200 may include a tunable laser light source 208 (hereafter "tunable laser 208") capable of emitting or generating electromagnetic radiation 210, as defined herein. The tunable laser 208 may be a laser capable of "tuning" or adjusting the output wavelength band of the electromagnetic radiation 210 during operation. In one embodiment, the tunable laser 208 may include an optical parametric oscillator (OPO).

The tunable laser 208 may be configured to emit the electromagnetic radiation 210 at a first angle 216a from a central axis in a direction towards the fabrication housing 206 and the ICE cores 202a-n arranged therein. In some embodiments, the electromagnetic radiation 210 may be unpolarized and pass through or otherwise interact with a polarizer 212, thereby producing polarized radiation 214. In other embodiments, the electromagnetic radiation 210 emitted from the tunable laser 208 may be polarized, thus the electromagnetic radiation 210 is equivalent and may be referred to as the polarized radiation 210, thus not requiring the intermediary polarizer 212. In any event, the polarized radiation 214 is conveyed to and eventually optically interacts with the ICE cores 202a-n.

In some embodiments, the fabrication housing 206 may contain a first sample window 220a and a second sample window 220b. The fabrication housing 206 may be a fabrication chamber or otherwise a chamber where the layers 102, 104 (FIG. 1) of each ICE core 202a-n may be progressively built or deposited to predetermined thicknesses. The sampling windows 220a,b may be made from a variety of transparent, rigid or semi-rigid materials that are configured to allow transmission of the polarized radiation 214 therethrough. For example, the sampling windows 220a,b may be made of glasses, plastics, semi-conductors, crystalline materials, polycrystalline materials, hot or cold-pressed powders, combinations thereof, or the like.

In at least one embodiment, the assembly 204 within the fabrication housing 206 may be generally circular and capable of rotation about a central axis, for example, in the direction A. The ICE cores 202a-n may be radially disposed about the assembly 204 for rotation therewith. The assembly 204 may also be capable of rotation in a direction opposite of direction A. While the assembly 204 is depicted as containing multiple ICE cores 202a-n, it will be appreciated that in some embodiments the assembly 204 may include only a single ICE core 202a-n.

In exemplary operation, the polarized radiation 214 may be transmitted through the first sample window 220a to optically interact with the ICE cores 202a-n, thereby producing an optically interacted radiation 222 reflected therefrom. The optically interacted radiation 222 may be emitted from each ICE core 202a-n at a second angle 216b from the central axis and exit the fabrication housing 206, as depicted, through a second sampling window 220b. Alternatively, the optically interacted radiation 222 may exit the fabrication housing 206 back through the first sample window 220a.

The optically interacted radiation 222 may be conveyed in a direction towards a rotating analyzer 225 and an optical transducer 224. The rotating analyzer 225 may be included in the measurement system 200 and otherwise used in conjunction with the optical transducer 224 prior to generation of the output signals 226a-n. As generally known in the art, ellipsometry measures the complex reflectance ratio (ρ) of a system, which may be parameterized by the amplitude component (ψ) and the phase difference (Δ). The polarization state of the light incident upon the sample may be decomposed into an (s) and a (p) component, where the (s) component is oscillating perpendicular to the plane of incidence and parallel to the sample surface, and the (p) component is oscillating parallel to the plane of incidence. The amplitudes of the s and p components, after reflection and normalized to their initial value, are typically denoted as $r_s$ and $r_p$, respectively. The angle of incidence is chosen close to the Brewster angle of the sample to ensure a maximal difference in $r_s$ and $r_p$. Ellipsometry measures the complex reflectance ratio, ρ (a complex quantity), which is the ratio of $r_p$ over $r_s$:

$$\rho = \frac{r_p}{r_s} = \tan(\psi)e^{-i\Delta} \quad \text{Equation (1)}$$

Thus, tan ($\psi$) is the amplitude ratio upon reflection, and $\Delta$ is the phase shift (difference). Since ellipsometry is measuring the ratio (or difference) of two values (rather than the absolute value of either), it is very robust, accurate, and reproducible. For instance, it is relatively insensitive to scatter and fluctuations, and requires no standard sample or reference beam.

The optical transducer 224 may be, for example, a thermal detector, such as a thermopile or photoacoustic detector, a semiconductor detector, a piezo-electric detector, a charge coupled device (CCD) detector, a video or array detector, a split detector, a photon detector (such as a photomultiplier tube), photodiodes, combinations thereof, or the like, or another detector known to those skilled in the art. The optical transducer 224 may be capable of measurements over a spectral region similar to that capable of being output from the tunable laser 208.

In some embodiments, the measurement system 200 may include an intensity filter 232 arranged along the optical path between the tunable laser 208 and the polarizer 212. In other embodiments, the intensity filter 232 may be arranged at any location along the optical path in between the tunable laser 208 and the optical transducer 224, such as directly preceding the optical transducer 224. The intensity filter 232 may be configured to reduce the intensity of the electromagnetic radiation 210 or optically interacted radiation 222 prior to detection by the optical transducer 224. Example intensity filters may include, but are not limited to, a physical mask, an aperture, or a neutral density (ND) filter. Advantageously, this power or intensity reduction by the intensity filter 232 may prevent oversaturation and possible damage to the optical transducer 224, while still allowing the full optical spectra of light to pass through.

Upon detecting the optically interacted radiation 222, the optical transducer 224 may generate corresponding output signals 226a-n related to each ICE core 202a-n. The output signals 226a-n may be in the form of a voltage, current, or combination thereof representing the nature of polarization of the optically interacted radiation 222 as a function of the angle modulated (i.e., the angle that the polarized radiation 214 was modulated upon optical interaction with each ICE core 202a-n).

In some applications, the output signals 226a-n may be conveyed to or otherwise received by a signal processor 228 communicably coupled to the optical transducer 224. The signal processor 228 may be a computer including a processor and a machine-readable storage medium having instructions stored thereon, which, when executed by the signal processor 228, cause the measurement system 200 to perform a number of operations, such as determining amplitude or phase difference between the output signal 226a-n and the polarized radiation 214. The machine-readable storage medium of the signal processor 228 may further include one or more stored models or pre-recorded data sets correlating amplitude and phase data of previously measured optically interacted radiation 222 to refractive indices, thereby enabling the signal processor 228 to compare the currently determined amplitude or phase of the optically interacted radiation 222 against the models and approximate the refractive index of the measured layers 102, 104 (FIG. 1) for each ICE core 202a-n.

The signal processor 228 may be configured to provide a resulting output signal 230 in real-time or near real-time, either wired or wirelessly, to an operator for consideration. The resulting output signal 230 may include information pertaining to the measured optically interacted radiation 222, such as amplitude or phase measurements, refractive index approximations, or layer thickness for each ICE core 202a-n.

To facilitate a better understanding of the distinguishing features of the present disclosure, the following examples of representative embodiments and advantages are given. In no way should the following examples be read to limit, or to define, the scope of the disclosure.

Figure 3:
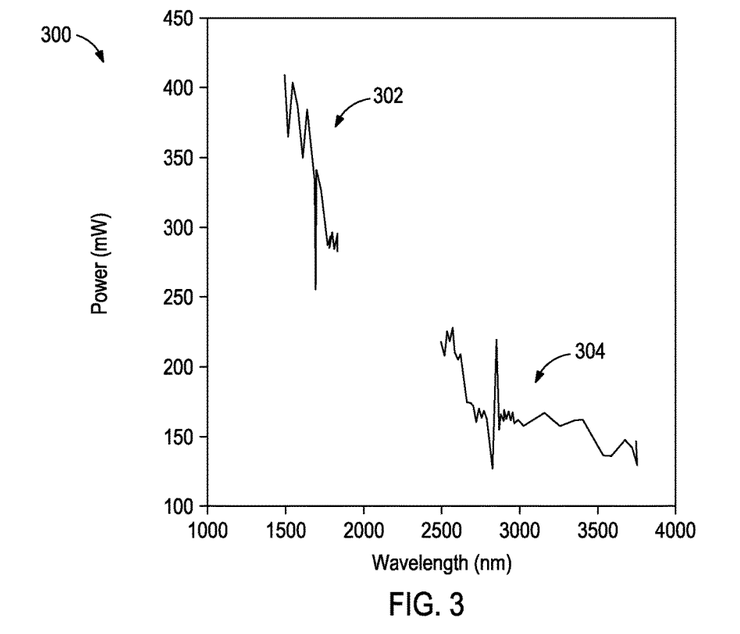
FIG. 3 illustrates a graph representing the output from a light source that may implement the principles of the present disclosure, according to one or more embodiments.

Referring now to FIG. 3, with continued reference to FIG. 2, illustrated is a graph 300 depicting output signals from the tunable laser 208 that may implement the principles of the present disclosure, according to one or more embodiments. As briefly discussed above, in one embodiment, the tunable laser 208 of the measurement system 200 may be a tunable laser implementing an optical parametric oscillator (OPO) (hereafter "OPO laser"). In at least one embodiment, the tunable laser 208 may be the Firefly-IR, commercially available through M Squared Lasers, Ltd. of Glasgow, Scotland. Briefly, the OPO converts an input laser wave (called a "pump") having a pump frequency (not shown) into two output signals of lower frequencies, called a signal output 302 at a first frequency and an idler output 304 at a second frequency, wherein the sum of the signal output 302 at the first frequency and the idler output 304 at the second frequency is equal to the pump frequency. In exemplary operation, the signal and idler output signals 302, 304 may be tuned by adjustment of the input pump frequency or by changing the phase matching properties of the nonlinear optical crystal. As depicted in the graph 300, the signal and idler output signals 302, 304 are graphed as measured by a power meter. Thus, the Y-axis represents power output and the X-axis represents the output wavelength.

Advantageously, OPO lasers may output electromagnetic radiation 210 over a broader spectral region than previously available in spectroscopic measurements, and doing so with a greater intensity. For example, as illustrated in the graph 300, the OPO laser idler output 304 may range from about 2500 nanometers at a power of about 225 mW (milliwatts) to about 3700 nanometers at a power of about 125 mW. In exemplary operation, only a subset of the overall output spectrum will be generated at a given time, for example, a wavelength band of 2-10 nm. However, this subset band of 2-10 nm may be tuned to scan an overall spectral range (e.g., the idler output 304 range of approximately 2500 to 3700 nanometers.)

The power of the idler output 304 (also called "light throughput," "light flux," or "energy density") in some cases may be four to ten orders of magnitude larger than traditional near-infrared (NIR) and mid-infrared (MIR) sources. For example, a blackbody source that operates at 2800K will output 0.05 mW of power at 3000 nm. Thus, as apparent, the broader spectral output region of a tunable laser or OPO laser enables improved limits of detection (i.e., detection over spectral regions previously unavailable) and the increased power may lead to a higher signal-to-noise (SNR) ratio, thereby increasing measurement sensitivity and accuracy.

A distinguishing feature resulting from the increased power and tunability of the tunable laser 208 may include improved capabilities of testing of low average transmittance ICE cores. For instance, one optical thin-film parameter is the percentage of light transmitted, otherwise known as transmittance (T). A lower transmittance (T) indicates that less light is transmitted through the layer(s) 102, 104 of the ICE cores 202a-n. ICE cores 202a-n having a low average light transmittance (T) may naturally result during the design process. These low transmittance numbers may be unsuitable for some applications, such as optically thick reservoir fluids and are thus discarded. The low transmittance ICE cores 202a-n, however, may be suitable in other respects, such as sensitivity, thin-film thickness, or number of layers, but are discarded due to the low transmittance producing optically interacted radiation 222 that is immeasurable due to a low SNR, or which falls below testing requirements. Thus, it can be appreciated that the power of a tunable laser, such as the OPO laser discussed above, may increase light transmission and thereby generate signals with a higher SNR that are measureable by the optical transducer 224.

Increased power of the tunable laser 208 may also enable improved sample interrogation path lengths. As well known in the art, transmittance is a function of path length, wherein transmittance decreases with increased path length. In other words, typically, as path length increases, light transmitted therethrough and to the optical transducer 224 decreases, thus eventually resulting in immeasurable signals. However, as the tunable laser 208 generates electromagnetic radiation 210 with more flux, more light will be transmitted over the path length. Therefore, the path length may be extended while still obtaining acceptable transmission rates at the optical transducer 224.

A further distinguishing feature of the present disclosure is the ability to perform in-situ measurements. Often, due to the physical geometry of the deposition system, such as the fabrication housing 206 of FIG. 2, a system configuration optimal for thin-film deposition may not be optimal for in-situ optical measurements. This may be due to the optical arrangement between the light source and the detector. For instance, if the light source is a traditional broadband light source, and light collection, steering and conditioning optics are used (e.g., lenses, windows and/or mirrors), the fabrication system arrangement may require long distances or path lengths to optically interact the source light with the sample under study and to receive said light with a detector arranged in the optical train. This may result in decreased SNR measurements.

As disclosed herein, the tunable laser 208 may reduce or eliminate these challenges, thus enabling in-situ ellipsometry. For example, typical lasers generate electromagnetic radiation 210 with a smaller output wavelength band (e.g., 2-10 nanometers) when compared to a broadband light source. Advantageously, the smaller band output of the typical laser is more focused, thus increasing the amount of light optically interacting with the sample (e.g., ICE cores 202a-n) and producing measurements with increased SNR. Similarly, tunable lasers have high light flux in a small beam profile, which allows for minimizing the number of required optics to be used and allow for longer light paths to be obtained with increased signal-to-noise. The increased power and broad wavelength range of a tunable laser, however, may further increase the SNR, thus reducing or eliminating the need for adjustment of the incident angle to obtain satisfactory measurements. Additionally, satisfactory measurements may be obtained by capabilities of tuning the incident wavelength band. Moreover, such tuning may be performed over a broader spectral region than previously available. In other embodiments, the fabrication system may require the angle of incidence between the sample and source light to be large enough to create a non-optimal spot size on the sample. Since the tunable laser 208 exhibits a minimal beam diameter, it is able to limit the spot size on the sample for high angles of incidence.

Figure 4:
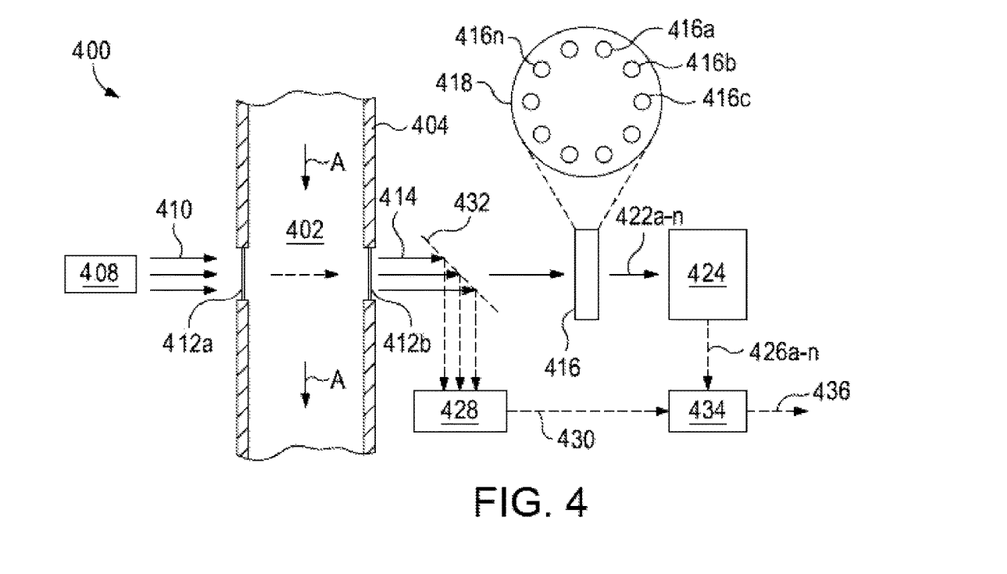
FIG. 4 illustrates an exemplary measurement system capable of determining characteristics of interest of a fluid, according to one or more embodiments.

Referring now to FIG. 4, with continued reference to FIGS. 1-3, illustrated is an exemplary measurement system 400 capable of determining characteristics of interest of a substance, such as a fluid 402, according to one or more embodiments. As illustrated, the measurement system 400 may be arranged to monitor the fluid 402, which may be contained or otherwise flowing within an exemplary flow path 404. The flow path 404 may be a flow line, a pipeline, a wellbore, an annulus defined within a wellbore, or any flow lines or pipelines extending to/from a wellbore. The fluid 402 present within the flow path 404 may be flowing from upstream to downstream as indicated by the arrows A, but could equally be stagnant, without departing from the scope of the disclosure. The flow path 404 may also be a container or part of a fluid testing system, possibly within a lab, again, where the fluid 402 may be flowing or stagnant while measurements are performed.

The measurement system 400 may be configured to determine characteristics of interest in the fluid 402, such as one or more chemical compositions or analytes present within the fluid 402. In some embodiments, the measurement system 400 may include a light source comprising a tunable laser 408 capable of emitting or generating electromagnetic radiation 410, as defined herein. The tunable laser 408 may be similar to the tunable laser 208 of FIG. 2, and therefore may be a laser capable of "tuning" or adjusting its output wavelength band of the electromagnetic radiation 410 during operation. In one embodiment, the tunable laser 408 may include an optical parametric oscillator (OPO), as generally described above.

The electromagnetic radiation 410 may be directed toward the fluid 402 and, more particularly, through the fluid 402 via a first sampling window 412a and a second sampling window 412b arranged radially-opposite the first sampling window 412a on the flow path 404. The first and second sampling windows 412a,b may be arranged adjacent to or otherwise in contact with the fluid 402 for detection purposes. The sampling windows 412a,b may be made from a variety of transparent, rigid or semi-rigid materials that are configured to allow transmission of the electromagnetic radiation 410 therethrough. For example, the sampling windows 412a,b may be made of glasses, plastics, semi-conductors, crystalline materials, polycrystalline materials, hot or cold-pressed powders, combinations thereof, or the like.

As the electromagnetic radiation 410 passes through the fluid 402 via the first and second sampling windows 412a,b, it optically interacts with the fluid 402 and optically interacted radiation 414 is subsequently generated. Those skilled in the art will readily recognize that alternative variations of the device 400 may allow the optically interacted radiation 414 to be generated by being reflected, scattered, diffracted, absorbed, emitted, or re-radiated by and/or from the fluid 402, without departing from the scope of the disclosure.

The optically interacted radiation 414 generated by the interaction with the fluid 402 may be directed to or otherwise be received by one or more ICE cores 416 (shown as ICE cores 416a, 416b, 416c, . . . 416n) or other thin-film devices arranged within the measurement system 400. Each ICE core 416a-n may be a spectral component substantially similar to the ICE core 100 described above with reference to FIG. 1. Accordingly, each ICE core 416a-n may be designed and otherwise configured to detect a particular and/or distinct characteristic of interest. In other embodiments, however, two or more of the ICE cores 416a-n may be configured to detect the same or substantially the same characteristic of interest. One of skill in the art will appreciate that, while ICE cores 416a-n are depicted and discussed herein, the ICE cores 416a-n may be replaced and the techniques disclosed herein may be equally applied to thin-film devices in general.

As illustrated, the ICE cores 416a-n may be strategically arranged on a movable assembly 418, such as a rotating disc, where the ICE cores 416a-n are radially disposed for rotation therewith. In other embodiments, however, the movable assembly 418 may be a linear array (not shown) having the ICE cores 416a-n strategically arranged thereon and laterally offset from each other, without departing from the scope of the disclosure. For illustrative purposes only, and not by limitation, the movable assembly 418 will be described with reference to the rotating disc depicted in FIG. 4.

As depicted, the ICE cores 416a-n are arranged about or near the periphery of the movable assembly 418 and circumferentially-spaced from each other. In various embodiments, the movable assembly 418 may be rotated at a frequency of about 0.1 RPM to about 2,000 RPM. In operation, the movable assembly 418 may rotate such that the individual ICE cores 416a-n may each be exposed to or otherwise optically interact with the optically interacted radiation 414 for a distinct brief period of time. Upon optically interacting with the optically interacted radiation 414, each ICE core 416a-n may be configured to produce modified electromagnetic radiation 422 (shown as modified electromagnetic radiation 422a, 422b, 422c, . . . 422n) corresponding to particular characteristics of interest of the fluid 402. In particular, the modified electromagnetic radiation 422a-n is an approximation of a regression vector corresponding to the characteristic of the fluid 402 for which each ICE core 416a-n was designed to detect.

Each beam of modified electromagnetic radiation 422a-n may be directed to and detected by an optical transducer 424, which may be configured to time multiplex the modified electromagnetic radiation 422a-n between the individually-detected beams and quantify each signal. The optical transducer 424 may be similar to the optical transducer 224 of FIG. 2, and therefore will not be described in detail again.

In some embodiments, the optical transducer 424 may be configured to produce individual output signals 426a-n corresponding to each beam of modified electromagnetic radiation 422a-n in real-time or near real-time. Each output signal 426a-n may be in the form of a voltage (or current) that corresponds to the particular characteristic of interest detected in the fluid 402 by each corresponding ICE core 416a-n. The output signals 426a-n returned by the optical transducer 424 are essentially the dot product of the optical interaction of the optically interacted radiation 414 with the respective ICE cores 416a-n as a function of the concentration of the characteristic of interest of the fluid 402 that each ICE core 416a-n is configured to detect. As such, the intensity of each output signal 426a-n produced by the optical transducer 424 and the concentration of the characteristics may be related, for example, directly proportional. In other embodiments, however, the relationship may correspond to a polynomial function, an exponential function, a logarithmic function, and/or a combination thereof.

In some embodiments, the measurement system 400 may include a second optical transducer 428, which may be similar to the first optical transducer 424 in that it may be any device capable of detecting electromagnetic radiation. The second optical transducer 428 may be used to detect radiating deviations that occur in conjunction with the intensity of the electromagnetic radiation 410 and which may cause various negative effects on the measurement system 400. In some embodiments, radiating deviations can occur as a result of a build-up of film or material on the sampling windows 412a,b, which has the effect of reducing the amount and quality of light ultimately reaching the first optical transducer 424. Without proper compensation, such radiating deviations could result in false readings and the output signals 426a-n would no longer be primarily or accurately related to the characteristic of interest.

To compensate for these types of undesirable effects, the second optical transducer 428 may be configured to generate a compensating signal 430 generally indicative of the radiating deviations of the electromagnetic radiation source 408, and thereby normalize the output signals 426a-n generated by the first optical transducer 424. As illustrated, the second optical transducer 428 may be configured to receive a portion of the optically interacted radiation 414 via a beamsplitter 432 in order to detect the radiating deviations. In other embodiments, however, the second optical transducer 428 may be arranged to receive electromagnetic radiation from any portion of the optical train in the measurement system 400 in order to detect the radiating deviations, without departing from the scope of the disclosure. In yet other embodiments, at least one of the ICE cores 416a-n may be a neutral element configured to simply pass the optically interacted radiation 414 without optical-interaction with the movable assembly 418. As a result, the neutral element may be configured to provide a neutral signal to the optical transducer 424 that may be substantially similar to the compensating signal 430.

In some applications, the output signals 426a-n and the compensating signal 430 may be conveyed to or otherwise received by a signal processor 434 communicably coupled to both the optical transducers 424, 428. The signal processor 434 may be a computer including a processor and a machine-readable storage medium having instructions stored thereon, which, when executed by the processor 434, cause the measurement system 400 to perform a number of operations, such as determining a characteristic of interest of the fluid 402. For instance, the concentration of each characteristic detected with the measurement system 400 can be fed into an algorithm operated by the signal processor 434. The algorithm can be part of an artificial neural network configured to use the concentration of each detected characteristic in order to evaluate the overall characteristic(s) or quality of the fluid 402.

The signal processor 434 may also be configured to computationally combine the compensating signal 430 with the output signals 426a-n in order to normalize the output signals 426a-n in view of any radiating deviations detected by the second optical transducer 428. Computationally combining the output and compensating signals 426, 430 may entail computing a ratio of the two signals 426, 430. For example, the concentration or magnitude of each characteristic determined using the measurement system 400 can be fed into an algorithm run by the signal processor 434. In real-time or near real-time, the signal processor 434 may be configured to provide a resulting output signal 436 corresponding to the characteristics of interest in the fluid 402. In some embodiments, the resulting output signal 436 may be conveyed, either wired or wirelessly, to an operator for consideration.

It should be noted that, while FIG. 4 depicts the movable assembly 418 as receiving the optically interacted radiation 414 as transmitted through the sampling windows 412a,b, the movable assembly 418 may equally be arranged at any point along the optical train of the measurement system 400, without departing from the scope of the disclosure. For example, in one or more embodiments, the movable assembly 418 may be arranged within the optical train prior to the first sampling window 412a and equally obtain substantially the same results. In yet other embodiments, the ICE cores 416a-n may generate the modified electromagnetic radiation 422 through reflection, instead of transmission therethrough.

Accordingly, the measurement system 400 may be able to monitor the fluid 402 and detect and report the concentration of characteristics corresponding to the design and manufacture of each ICE core 416a-n. It will be appreciated that any number of ICE cores 416a-n may be used in the measurement system 400, thereby providing data corresponding to an equal number of characteristics of the fluid 402.

As will be appreciated, implementation of a tunable laser may prove useful or otherwise relevant in measuring the fluid 402, where the sample spectrum of the fluid 402 contains narrow features. As indicated above, typical light sources output a broad spectrum of light simultaneously. Thus, the modified electromagnetic radiation 422a-n received by the optical transducers 424, 428 contains information pertaining to the entire spectrum. The tunable laser 408, however, operates by way of outputting a wavelength band (e.g., 2-10 nm) of high light flux, and scanning that band over a broad spectral range (e.g., 2500 to 3700 nm). As a result, the optical transducers 424, 428 receive modified electromagnetic radiation 422a-n pertaining only to the wavelength band currently being output by the tunable laser 408. Therefore, the signal processor 434 may perform addition or other calculations (e.g., performing a digital regression) either in real-time as it receives the output signal(s) 426a-n, or after the full spectral range has been scanned.

Advantageously, an operator may decrease testing time by tuning the tunable laser 408 and testing only those wavelengths of interest in a sample (i.e., fluid 402) under investigation, instead of scanning the entire spectral range available by the tunable laser 408. Such a process may be characterized as scanning one or more discontinuous wavelengths. Thus, implementation of a tunable laser 408 as the light source may result in more accurate measurements within a more reasonable (i.e., less) testing time. This is due to the fact that redundant information in non-contributing wavelengths can be ignored by scanning to only relevant wavelengths. As will be appreciated, ignoring these non-useful wavelengths reduces noise in the measurement of the property of interest.

Figure 5A:
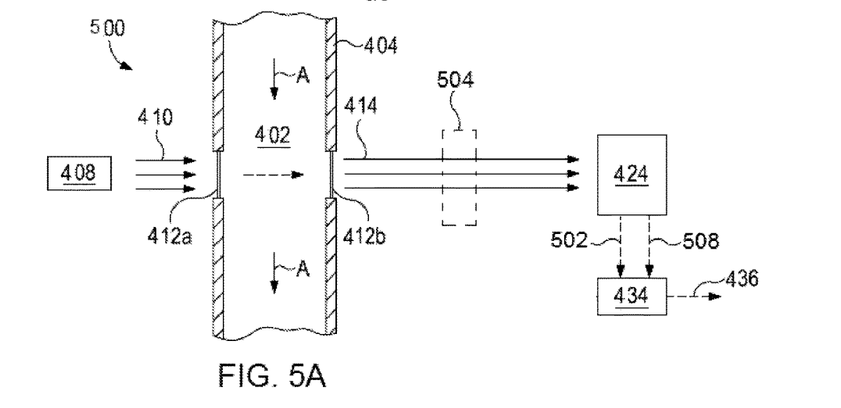
FIGS. 5A-5C illustrate an exemplary measurement system capable of determining the transmittance of a fluid, according to one or more embodiments.
Figure 5B:
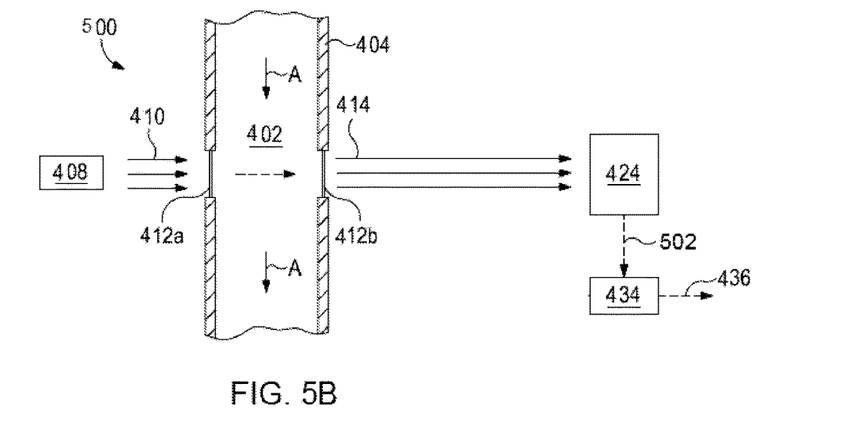
Figure 5C:
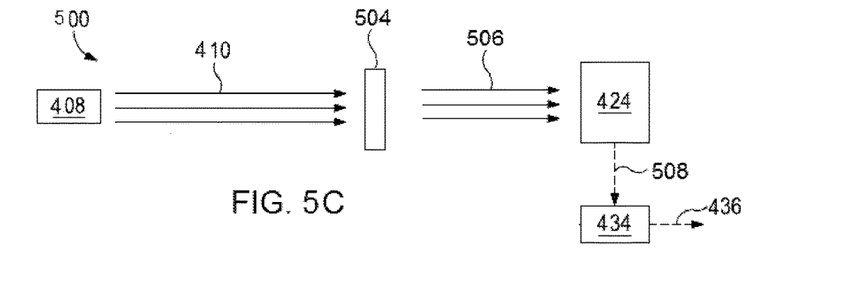

Referring now to FIGS. 5A-5C, illustrated are progressive views of a measurement system 500 that can be used for determining characteristics of fluids, according to one or more embodiments. The measurement system 500 may be similar in some respects to the measurement system 400 of FIG. 4, and therefore may be best understood with reference thereto where like numerals indicate like elements that will not be described again. The measurement system 500 may employ the tunable laser 408 in order to ascertain or more accurately measure characteristics of the fluid 402 and, more particularly, the transmittance of the fluid 402.

Transmittance ($T_\lambda$) of a sample (i.e., the fluid 402) may be defined as the ratio of intensity of light ($I_\lambda$) from the sample divided by the intensity of incident light from the tunable laser ($I_{0\lambda}$) 408 as a function of wavelength ($\lambda$). In other words, $T_\lambda=(I_\lambda/I_{0\lambda})$. However, the intensity of light ($I_{0\lambda}$) from the tunable laser 408 may be too intense for the optical transducer 424, thereby possibly saturating and damaging the optical transducer 424. To mitigate these effects, an intensity filter 504 may be used or implemented in the system 500 to reduce the light intensity of the tunable laser 408 by a predetermined magnitude ($nd_\lambda$) at that wavelength $\lambda$. Accounting for such, the transmittance equation may become $T_\lambda=((nd_\lambda)*(I_\lambda/I_{0\lambda}))$. Thus, the corrected transmittance is proportional to the amount of attenuation from the intensity filter 504.

FIG. 5A illustrates one embodiment of the measurement system 500 as a whole, including the tunable laser 408, the fluid 402 within the flow path 404, the intensity filter 504 (shown in dashed), the optical transducer 424, and the signal processor 434, all arranged in the optical train. However, for clarity of exemplary operation, FIG. 5B depicts one embodiment of the measurement system 500 as configured to measure the intensity of light ($I_\lambda$) from the fluid sample 402 and FIG. 5C depicts another embodiment the measurement system 500 as configured to measure the intensity of light from the tunable laser ($I_{0\lambda}$) 408.

Referring first to FIG. 5B, in order to measure the light from the fluid 402, the measurement system 500 may include the tunable laser 408, the fluid 402 within the flow path 404, the optical transducer 424, and the signal processor 434. The tunable laser 408 may be capable of emitting electromagnetic radiation 410 in a direction towards the flow path 404. The electromagnetic radiation 410 may travel through the sample windows 412a,b to optically interact with the fluid 402. Again, in at least one embodiment, the flow path 404 may also be a container or part of a fluid testing system, possibly within a lab, where the fluid 402 may be flowing or stagnant while measurements are performed.

As the electromagnetic radiation 410 passes through the fluid 402, it optically interacts therewith and optically interacted radiation 414 is subsequently generated. Those skilled in the art will readily recognize that alternative variations of the device 400 may allow the optically interacted radiation 414 to be generated by being reflected, scattered, diffracted, absorbed, emitted, or re-radiated by and/or from the fluid 402, without departing from the scope of the disclosure. The optically interacted radiation 414 may be directed to or otherwise be received by the optical transducer 424.

In some embodiments, the optical transducer 424 may be configured to produce a sample output signal ($I_\lambda$) 502 in the form of a voltage (or current), the sample output signal ($I_\lambda$) 502 corresponding to the optically interacted radiation 414. In some embodiments, the sample output signal ($I_\lambda$) 502 may be conveyed to or otherwise received by the signal processor 434, and the signal processor 434 may be configured to save the sample output signal ($I_\lambda$) 502 in memory (not shown) for determining the transmittance of the fluid 402.

Referring now to FIG. 5C, illustrated is the measurement system 500 as configured to determine a reference measurement. Similar to FIG. 5B, the measurement system includes the tunable laser 408, the optical transducer 424, and the signal processor 434. However, unlike FIG. 5B, the measurement system 500 no longer includes the fluid 402 and fluid path 404, but instead includes an intensity filter 504 arranged along the optical path between the tunable laser 408 and the optical transducer 424. The intensity filter 504 may be similar to the intensity filter 232 of FIG. 2, and therefore will not be described again in detail.

As depicted, the intensity filter 504 is in optical communication with the tunable laser 408 and is therefore able to receive the electromagnetic radiation 410 therefrom. As indicated above, the intensity filter 504 may be configured to reduce the intensity of the electromagnetic radiation 410 by a predetermined magnitude ($nd_\lambda$), thus generating reduced intensity electromagnetic radiation 506. For example, the intensity filter 504 may reduce the intensity by 10%. However, it will be appreciated that the intensity filter 504 may alternatively reduce the intensity by more or less than 10%, without departing from the scope of the disclosure. Moreover, while only one intensity filter 504 is depicted, embodiments are contemplated herein that employ more than one intensity filter 504 combined to reduce the intensity of the electromagnetic radiation 410.

The reduced intensity electromagnetic radiation 506 may be conveyed to or otherwise received by the optical transducer 424 communicably coupled to the intensity filter 504. Thus, advantageously, the power or intensity reduction by the intensity filter 504 may prevent oversaturation and possible damage to the optical transducer 424, while still allowing the full optical spectra of light to pass therethrough.

The optical transducer 424 may be communicably coupled to the signal processor 434 and configured to generate a reference output signal ($I_{0\lambda}$) 508 thereto corresponding to the measured reduced intensity radiation 506. The signal processor 434 may then be configured to save the reference output signal ($I_{0\lambda}$) 508 in memory (not shown) for later use in determining the transmittance of the fluid 402.

Referring again to FIG. 5A, the signal processor 434 is depicted as being communicably coupled to the optical transducer 424 and configured to receive the detected incident output signal ($I_\lambda$) 502 and reference output signal ($I_{0\lambda}$) 508. Once the signal processor 434 receives the incident output signal ($I_\lambda$) 502 and reference output signal ($I_{0\lambda}$) 508, or otherwise has them stored in memory, the transmittance of the fluid 402 at a first time period and for a first wavelength ($\lambda$) may then be calculated using the equation $T_\lambda = ((nd_\lambda) * (I_\lambda/I_{0\lambda}))$. Advantageously, due to the increased intensity of light flux from the tunable laser 408, previously unavailable transmittance calculations of optically thick fluids may now may be determinable.

Various known or expected wavelengths (i.e., discontinuous wavelengths or spectra) of interest may then be scanned using the tunable laser 408 and the various resulting output signals derived therefrom may also be stored in memory or otherwise transmitted to a computer for processing. An operator may be able to determine one or more characteristics of the fluid 402 from such output signals by applying a regression analysis to the output signals. In some embodiments, this may be accomplished by placing a filter (not shown) in front of the optical transducer 424, where the filter exhibits a specific or appropriate weighting value for each wavelength. In other embodiments, the appropriate regression vector for each wavelength may be stored in memory and accessed for the calculation.

One of skill in the art will appreciate the various arrangements and configurations that the measurement system 500 may incorporate, without departing from the scope of the disclosure. For example, in other embodiments, the intensity filter 504 of FIG. 5C may be left in the measurement system 500 during measurement of the incident output signal (I) 502 (described in FIG. 5B), but simply reduce the intensity by 0% (e.g., an aperture being fully open), thus not altering or affecting radiation traveling along the optical path. Alternatively, the measurement system 500 may include two independent paths for measuring the incident output signal (I) 502 and reference output signal ($I_0$) 508, either independently or simultaneously.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Embodiments disclosed herein include:

A. A system that includes a tunable laser capable of generating electromagnetic radiation, one or more thin-film devices arranged to receive the electromagnetic radiation, each thin-film device including one or more optical layers deposited on a corresponding substrate and configured to generate optically interacted radiation upon receiving the electromagnetic radiation, and an optical transducer arranged to receive the optically interacted radiation from each of the one or more thin-film devices and configured to generate output signals corresponding to the optically interacted radiation received from each of the one or more thin-film devices.

B. A method that includes generating electromagnetic radiation from a tunable laser, receiving the electromagnetic radiation with one or more thin-film devices, each of the one or more thin-film devices including one or more optical layers deposited on a corresponding substrate, generating optically interacted radiation from each of the one or more thin-film devices upon receiving the electromagnetic radiation, receiving the optically interacted radiation with an optical transducer, and generating output signals with the optical transducer corresponding to the optically interacted radiation received from each of the one or more thin-film devices.

C. A system that includes a tunable laser capable of generating electromagnetic radiation, a fluid within a flow path and configured to optically interact with the electromagnetic radiation, thereby generating optically interacted radiation, one or more thin-film devices arranged to receive the optically interacted radiation, each thin-film device including one or more optical layers deposited on a corresponding substrate and configured to generate modified electromagnetic radiation upon optically interacting with the optically interacted radiation, and an optical transducer arranged to receive the modified electromagnetic radiation from each of the one or more thin-film devices and configured to generate corresponding output signals therefrom.

D. A method that includes generating electromagnetic radiation from a tunable laser, optically interacting the electromagnetic radiation with a fluid arranged within a flow path and thereby generating optically interacted radiation, optically interacting the optically interacted radiation with a thin-film device and thereby generating modified electromagnetic radiation, the thin-film device including one or more optical layers deposited on a substrate, receiving the modified electromagnetic radiation with an optical transducer, and generating output signals with the optical transducer corresponding to the modified electromagnetic radiation received from each of the one or more thin-film devices.

E. A system that includes a tunable laser capable of generating electromagnetic radiation, a fluid within a flow path and configured to optically interact with the electromagnetic radiation, thereby generating optically interacted radiation, an interference filter configured to interact with the electromagnetic radiation and thereby generate reduced intensity electromagnetic radiation, an optical transducer arranged to receive at the optically interacted radiation and generate a corresponding first output signal, and further configured to receive the reduced intensity electromagnetic radiation and generate a corresponding second output signal, and a signal processor configured to receive the first and second output signals from the optical transducer and determine a characteristic of the fluid based on the first and second output signals.

F. A method that includes generating electromagnetic radiation from a tunable laser, optically interacting the electromagnetic radiation with a fluid within a flow path and thereby generating optically interacted radiation, optically interacting the electromagnetic radiation with an interference filter and thereby generating reduced intensity electromagnetic radiation, receiving the optically interacted radiation and the reduced intensity electromagnetic radiation with an optical transducer, generating a first output signal with the optical transducer corresponding to the optically interacted radiation, generating a second output signal with the optical transducer corresponding to the reduced intensity electromagnetic radiation, receiving the first and second output signals with a signal processor, and determining a characteristic of interest of the fluid with the signal processor based on the first and second output signals.

Each of embodiments A, B, C, D, E, and F may have one or more of the following additional elements in any combination: Element 1: further comprising a polarizer configured to receive and polarize the electromagnetic radiation. Element 2: wherein the one or more thin-film devices are optical thin-films. Element 3: wherein the optical thin-films are integrated computational elements. Element 4: wherein the tunable laser further comprises an optical parametric oscillator. Element 5: further comprising an intensity filter arranged in an optical path between the tunable laser and the optical transducer. Element 6: wherein the one or more thin-film devices are arranged on an assembly. Element 7: wherein the assembly is capable of moving relative to the source and detector in at least one direction in order to expose the one or more thin-films devices to the electromagnetic radiation. Element 8: wherein the one or more thin-film devices are arranged within a fabrication housing. Element 9: wherein the fabrication housing further includes one or more sample windows configured to allow the electromagnetic radiation and optically interacted radiation to pass therethrough. Element 10: further comprising a signal processor configured to receive the output signals and determine one or more parameters corresponding to the one or more thin-film devices. Element 11: wherein the signal processor includes a machine-readable storage medium that includes at least one model or data set capable of correlating amplitude and phase data of optically interacted radiation to refractive indices, and wherein the signal processor is configured to determine the one or more parameters by comparing the output signals with the at least one model or data set. Element 12: wherein the signal processor is further configured to output a resulting output signal indicative of the one or more parameters of the one or more thin-film devices.

Element 13: further comprising receiving and polarizing the electromagnetic radiation with a polarizer. Element 14: further comprising tuning the electromagnetic radiation with an optical parametric oscillator associated with the tunable laser. Element 15: further comprising reducing an intensity of the electromagnetic radiation or the optically interacted radiation with an intensity filter arranged in an optical path between the tunable laser and the optical transducer. Element 16: further comprising receiving the output signals with a signal processor communicably coupled to the optical transducer, the signal processor comprising a machine-readable storage medium including at least one model or data set correlating amplitude and phase data of optically interacted radiation to refractive indices, determining one or more parameters of each thin-film device with the signal processor based on the output signals and the at least one model or data set correlating amplitude and phase data of optically interacted radiation to refractive indices, and generating resulting output signals from the signal processor corresponding to the one or more parameters. Element 17: wherein determining the one or more parameters of each thin-film device comprises determining an amplitude and a phase of the optically interacted radiation. Element 18: wherein determining the one or more parameters of each thin-film device comprises determining a refractive index of the one or more optical layers by comparing the output signals to the at least one model or data set of the machine-readable storage medium. Element 19: wherein determining the one or more parameters of each thin-film device comprises determining a thickness of the one or more optical layers of the one or more thin-film devices. Element 20: further comprising scanning a spectrum of wavelengths with the tunable laser and thereby altering the output signals, receiving the altered output signals correlating to the scanned spectrum with the signal processor, and storing at least a portion of the altered output signals as one of the one or more models or data sets.

Element 21: wherein the one or more thin-film devices are optical thin-films. Element 22: wherein the optical thin-films are integrated computational elements. Element 23: wherein the tunable laser further comprises an optical parametric oscillator. Element 24: wherein the one or more thin-film devices are arranged on an assembly. Element 25: wherein the assembly is capable of rotating in at least one direction in order to expose the one or more thin-films devices to the electromagnetic radiation. Element 26: further comprising a signal processor configured to receive the output signals and determine one or more characteristics of interesting of the fluid. Element 27: wherein the signal processor is further configured to output a resulting output signal indicative of the one or more characteristics of interesting of the fluid. Element 28: wherein the electromagnetic radiation is generated over one or more discontinuous wavelengths. Element 29: wherein the flow path is one of a flow line, a pipeline, a wellbore, an annulus defined within a wellbore, and flow lines or pipelines extending to/from a wellbore.

Element 30: wherein generating the electromagnetic radiation from the tunable laser comprises generating the electromagnetic radiation over one or more discontinuous wavelengths. Element 31: where the one or more discontinuous wavelengths are known or expected wavelengths of interest. Element 32: wherein the tunable laser further comprises an optical parametric oscillator. Element 33: wherein the thin-film devices are arranged on an assembly capable of rotating, the method further comprising rotating the thin-film devices. Element 34: further comprising receiving the output signals with a signal processor and generating a resulting output signal therefrom indicative of the one or more characteristics of interesting of the fluid.

Element 35: wherein the tunable laser further comprises an optical parametric oscillator. Element 36: wherein the characteristic of the fluid is a transmittance of the fluid. Element 37: wherein the flow path is one of a flow line, a pipeline, a wellbore, an annulus defined within a wellbore, and flow lines or pipelines extending to/from a wellbore. Element 38: wherein the interference filter is one of a filter, an aperture, and an iris. Element 39: further comprising a resulting output signal generated by the signal processor corresponding to the characteristic of the fluid.

Element 40: wherein determining the characteristic of interest of the fluid further comprises calculating a transmittance of the fluid. Element 41: wherein the interference filter is one of a filter, an aperture, and an iris. Element 42: wherein the tunable laser is an optical parametric oscillator. Element 43: further comprising transmitting the first and second output signals at different times. Element 44: further comprising generating a resulting output signal from the signal processor, the resulting output signal being indicative of the characteristic of interest of the fluid.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A system, comprising:
a tunable laser capable of generating electromagnetic radiation;
one or more thin-film devices arranged to receive a portion of the electromagnetic radiation, each thin-film device including one or more optical layers deposited on a corresponding substrate and configured to generate optically interacted radiation upon receiving the electromagnetic radiation;
a filter configured to receive another portion of the electromagnetic radiation that is separate from the optically interacted radiation to generate reduced intensity electromagnetic radiation, the reduced intensity electromagnetic radiation comprising an intensity of the another portion of the electromagnetic radiation reduced by a predetermined magnitude by the filter; and
an optical transducer arranged to receive the optically interacted radiation from each of the one or more thin-film devices and configured to generate output signals corresponding to the optically interacted radiation received from each of the one or more thin-film devices and output signals corresponding to the reduced intensity electromagnetic radiation.

2. The system of claim 1, further comprising a polarizer configured to receive and polarize the electromagnetic radiation.

3. The system of claim 1, wherein the one or more thin-film devices are optical thin-films.

4. The system of claim 3, wherein the optical thin-films are integrated computational elements.

5. The system of claim 1, wherein the tunable laser further comprises an optical parametric oscillator.

6. The system of claim 1, wherein the one or more thin-film devices are arranged on an assembly.

7. The system of claim 6, wherein the assembly comprises a rotatable structure that, when rotated, moves the one or more thin-film devices in at least one direction in order to expose the one or more thin-film devices to the electromagnetic radiation.

8. The system of claim 1, further comprising a signal processor configured to receive the output signals and determine one or more parameters corresponding to the one or more thin-film devices.

9. The system of claim 8, wherein the signal processor includes a machine-readable storage medium that includes at least one model or data set capable of correlating amplitude and phase data of optically interacted radiation to refractive indices, and wherein the signal processor is configured to determine the one or more parameters by comparing the output signals with the at least one model or data set.

10. The system of claim 8, wherein the signal processor is further configured to output a resulting output signal indicative of the one or more parameters of the one or more thin-film devices.

11. A method, comprising:
generating electromagnetic radiation from a tunable laser;
receiving a portion of the electromagnetic radiation with one or more thin-film devices, each of the one or more thin-film devices including one or more optical layers deposited on a corresponding substrate;
generating optically interacted radiation from each of the one or more thin-film devices upon receiving the electromagnetic radiation;
receiving another portion of the electromagnetic radiation with a filter;
generating reduced intensity electromagnetic radiation from the filter, the reduced intensity electromagnetic radiation comprising an intensity of the another portion of the electromagnetic radiation reduced by a predetermined magnitude;
receiving the optically interacted radiation and the reduced intensity electromagnetic radiation with an optical transducer; and
generating output signals with the optical transducer corresponding to the optically interacted radiation received from each of the one or more thin-film devices and output signals corresponding to the reduced intensity electromagnetic radiation.

12. The method of claim 11, further comprising receiving and polarizing the electromagnetic radiation with a polarizer.

13. The method of claim 11, further comprising tuning the electromagnetic radiation with an optical parametric oscillator associated with the tunable laser.

14. The method of claim 11, further comprising:
receiving the output signals with a signal processor communicably coupled to the optical transducer, the signal processor comprising a machine-readable storage medium including at least one model or data set correlating amplitude and phase data of optically interacted radiation to refractive indices;
determining one or more parameters of each thin-film device with the signal processor based on the output signals and the at least one model or data set correlating amplitude and phase data of optically interacted radiation to refractive indices; and
generating resulting output signals from the signal processor corresponding to the one or more parameters.

15. The method of claim 14, wherein determining the one or more parameters of each thin-film device comprises determining an amplitude and a phase of the optically interacted radiation.

16. The method of claim 14, wherein determining the one or more parameters of each thin-film device comprises determining a refractive index of the one or more optical layers by comparing the output signals to the at least one model or data set of the machine-readable storage medium.

17. The method of claim 14, wherein determining the one or more parameters of each thin-film device comprises determining a thickness of the one or more optical layers of the one or more thin-film devices.

18. The method of claim 14, further comprising:
scanning a spectrum of wavelengths with the tunable laser and thereby altering the output signals;
receiving the altered output signals correlating to the scanned spectrum with the signal processor; and
storing at least a portion of the altered output signals as one of the one or more models or data sets.

19. A system, comprising:
a tunable laser capable of generating electromagnetic radiation;
a fluid within a flow path and configured to optically interact with a portion of the electromagnetic radiation, thereby generating optically interacted radiation;
a filter configured to reduce the intensity of another portion of the electromagnetic radiation to generate reduced intensity electromagnetic radiation, the reduced intensity electromagnetic radiation comprising an intensity of the another portion of the electromagnetic radiation reduced by a predetermined magnitude;
one or more thin-film devices arranged to receive the optically interacted radiation, each thin-film device including one or more optical layers deposited on a corresponding substrate and configured to generate modified electromagnetic radiation upon optically interacting with the optically interacted radiation; and
an optical transducer arranged to receive the reduced intensity electromagnetic radiation and the modified electromagnetic radiation from each of the one or more thin-film devices and configured to generate corresponding output signals therefrom.

20. A system, comprising:
a tunable laser capable of generating electromagnetic radiation;
a fluid within a flow path and configured to optically interact with the electromagnetic radiation, thereby generating optically interacted radiation;
an optical element configured to interact with the electromagnetic radiation and thereby generate reduced intensity electromagnetic radiation, the reduced intensity electromagnetic radiation comprising an intensity of the electromagnetic radiation reduced by a predetermined magnitude;
an optical transducer arranged to receive at the optically interacted radiation and generate a corresponding first output signal, and further configured to receive the reduced intensity electromagnetic radiation and generate a corresponding second output signal; and
a signal processor configured to receive the first and second output signals from the optical transducer and determine a characteristic of the fluid based on the first and second output signals.

21. The system of claim 20, wherein the optical element is an interference filter.

\* \* \* \* \*

UNITED STATES PATENT AND TRADEMARK OFFICE
CERTIFICATE OF CORRECTION

PATENT NO. : 10,145,675 B2
APPLICATION NO. : 14/408354
DATED : December 4, 2018
INVENTOR(S) : David L. Perkins It is certified that error appears in the above-identified patent and that said Letters Patent is hereby corrected as shown below:

In Column 9, Line 11, delete "measureable" and insert --measurable--

Signed and Sealed this
Twelfth Day of March, 2019

Andrei Iancu
*Director of the United States Patent and Trademark Office*